(12) United States Patent
Parker et al.

(10) Patent No.: US 12,102,349 B2
(45) Date of Patent: Oct. 1, 2024

(54) CIRCUMCISION DEVICE

(71) Applicant: INNOVATIVE MEDICAL TECHNOLOGY (PTY) LTD, Cape Town (ZA)

(72) Inventors: Cyril Norman Parker, Fresnaye (ZA); Elisabeth Regina Parker, Fresnaye (ZA)

(73) Assignee: Innovative Medical Technology (Pty) Ltd, Cape Town (ZA)

(*) Notice: Subject to any disclaimer, the term of this patent is extended or adjusted under 35 U.S.C. 154(b) by 390 days.

(21) Appl. No.: 17/612,509

(22) PCT Filed: May 19, 2020

(86) PCT No.: PCT/ZA2020/050026
§ 371 (c)(1),
(2) Date: Nov. 18, 2021

(87) PCT Pub. No.: WO2020/237264
PCT Pub. Date: Nov. 26, 2020

(65) Prior Publication Data
US 2022/0265299 A1 Aug. 25, 2022

(30) Foreign Application Priority Data

May 20, 2019 (ZA) .................................. 2019/03137

(51) Int. Cl.
*A61B 17/326* (2006.01)
(52) U.S. Cl.
CPC ................................ *A61B 17/326* (2013.01)
(58) Field of Classification Search
CPC ............... A61B 17/32; A61B 17/3205; A61B 17/32053; A61B 17/326;
(Continued)

(56) References Cited

U.S. PATENT DOCUMENTS 4,961,728 A 10/1990 Kosinski
5,127,906 A 7/1992 Landry, Jr. et al.
(Continued)

FOREIGN PATENT DOCUMENTS

CN 106667551 A 5/2017
CN 206995311 U 2/2018
(Continued)

OTHER PUBLICATIONS

International Search Report and Written Opinion for corresponding PCT/ZA2020/050026 mailed Aug. 13, 2020, 10 Pages.
(Continued)

*Primary Examiner* — Robert A Lynch
(74) *Attorney, Agent, or Firm* — Armstrong Teasdale LLP

(57) ABSTRACT

Described herein is a circumcision device including a support having a glans penis locating member mountable thereto. The support is provided with at least one pillar that includes a proximal end and a distal end, the distal end being fastened to a crush plate. The pillar facilitates movement of the crush plate relative to the support. A locking device is moveable between a locked position and an unlocked position, such that axial movement of the pillar is inhibited in the locked position and enabled in the unlocked position. The locking device is at least partially hidden by the support. A blocking device is interposed between the support and the crush plate to block movement of the crush plate towards the support past a predefined point to inhibit the locking device from becoming exposed.

10 Claims, 8 Drawing Sheets

(58) Field of Classification Search
CPC .. A61B 2017/0023; A61B 2017/00367; A61B 2017/00477; A61B 2017/320052; A61B 90/03; A61B 2090/034; A61B 2090/0814
See application file for complete search history.

(56) References Cited

U.S. PATENT DOCUMENTS

| | | | |
|---|---|---|---|
| 6,416,323 | B1 | 7/2002 | Grenfell et al. |
| 2007/0149985 | A1* | 6/2007 | Cole ................ A61B 17/32053 600/566 |
| 2010/0016803 | A1 | 1/2010 | Liversidge |
| 2014/0296741 | A1* | 10/2014 | Austen ............. A61B 17/32002 600/567 |
| 2017/0119422 | A1* | 5/2017 | Van Wyk ............ A61B 17/326 |

FOREIGN PATENT DOCUMENTS

| | | | |
|---|---|---|---|
| WO | 2009091235 | A2 | 7/2009 |
| WO | 2015155724 | A1 | 10/2015 |
| WO | 2018130983 | A1 | 7/2018 |
| WO | 2014094005 | A1 | 6/2021 |

OTHER PUBLICATIONS

First Office Action for Chinese Application No. 202080045021.9 issued on Dec. 30, 2023, 9 pages.

* cited by examiner

CIRCUMCISION DEVICE

CROSS-REFERENCE TO RELATED APPLICATION

This application is a U.S. National Phase Application of International Patent Application No. PCT/ZA2020/050026, filed May 19, 2020, which claims priority from South African provisional patent application number 2019/03137 filed on 20 May 2019, which is incorporated by reference herein.

FIELD OF THE INVENTION

This invention relates to a circumcision device or aid that facilitates surgical circumcisions. More particularly, but not exclusively, this invention relates to a circumcision device or aid which is a single use device that resists tampering to inhibit transfer of infection.

BACKGROUND TO THE INVENTION

Circumcision of male persons is carried out for a number of different reasons including religious and health reasons.

Human immunodeficiency virus (HIV) is a blood-borne virus that affects millions of people each year. The majority of worldwide infections have occurred in sub-Saharan Africa, where 19.2 million individuals were reported HIV-positive in 2014. Male circumcision has been shown to decrease a man's chances of contracting HIV from an HIV positive female partner by a significant percentage. Based on this, circumcision is used as a method of combating the spread of HIV and has the potential to avert many new infections each year.

The circumcision process has remained largely unaltered for the past few decades. Commonly, a Gomco clamp that has been in use since 1935 is used as a surgical assist instrument. Alternatively, a freehand incision (classical) may be used usually by a surgeon to perform a circumcision using a scalpel that is followed by the introduction of sutures. The Gomco clamp works by exerting a crushing force on the foreskin in a crush zone created in a gap between the divergent outer crushing surface of a glans penis locating member (termed a bell in the instance of the Gomco clamp) and a periphery of a crush aperture in a crush plate so that the skin can be cut away after a period of time. This clamping creates a "hemostatic seal" along the cut edge, which obviates the need for sutures. Whilst the Gomco device provides a simple, safe method for circumcision, it is not necessarily ideal for the large numbers of circumcision procedures targeted in Sub-Saharan Africa.

Many circumcision devices including the Gomco clamp are reusable devices and the WHO (World Health Organization) recommends that circumcision devices should actively resist attempts to be reused. Reusing circumcision devices is dangerous, especially when the device is not used by a trained medical practitioner, or when the device is not properly sterilized after use. This may lead to the inadvertent spread of HIV, other viruses, diseases, or infections. Other circumcision devices include rings and clamps, like the Prepex, Shangring, Tara KLamp, Ismail clamp, Plastibell and Alisklamp. Plastic devices generally need to be left on the body for 5 to 7 days after which time they have to be removed. A device that is left in place for an extended period of time may lead to complications with scheduling follow-up visits for the removal of the device. Additionally, there is a concern that the popularity of the entire circumcision program could be affected by a foul smell that may accompany wearing the device as the skin begins to die and decompose which increases the risk of infection with bacteria such as tetanus. Moreover, it is possible that patients may remove these devices themselves prematurely which can have dangerous consequences. Once removed, these devices may also be reused unscrupulously.

As regards published material describing attempts to fulfill the requirements of a single use circumcision device, international publication number WO2014094005 ("WO'005") describes a circumcision device having a central glans penis locating member having a divergent outer surface cooperating with a crushing surface of an aperture in a crush plate. The locating member is axially moveable relative to the crush plate, so that a gap between the divergent outer surface and crushing surface of the aperture in the crush plate can be varied to effect crushing of a prepuce that is positioned between them in well-known manner. The means for effecting axial movement is provided by a pair of diametrically opposite screw threaded pillars located on opposite sides of a support whereon the central glans penis locating member is located. In this instance, single use is achieved by utilising internal clips and corresponding protrusions of the support. When the clips are moved over the protrusions, the diametrically opposite screw threaded members are no longer able to be retracted from the support. After circumcision is performed, the glans penis locating member is dislocated or released from the support. The clips may then prevent the glans penis locating member to be subsequently mounted back onto the support, or even when the locating member is somehow mounted on the support again, the gap between the crushing surface and crush aperture would not be large enough to receive a subsequent prepuce therethrough. However, while the clips described in WO'005 may facilitate non-reusability, unscrupulous parties may attempt to remove the clips against the manufacturer's instructions, and then attempt to reuse the device.

A similar device is described in international publication number WO2015155724 ("WO'724") in which relative axial movement is achieved using a single screw threaded wing nut cooperating with a central tubular body having a glans penis locating end and an opposite operating end at which the wing nut is located. An attempt is made to prevent reuse of the device by providing the central tubular body with wedged members such that the wedged members "click" onto a support plate (termed a "base plate" in WO'724) after circumcision is performed. However, an unscrupulous party may easily utilise manual manipulation, long-nose pliers, or the like to urge the wedged members inward to undo them and may then remove the central tubular body to reuse the device in its entirety. Moreover, even if the wedged members are not undone, and if removable clips of the device are removed, a gap between the central tubular body and a crush plate may be large enough to receive a subsequent prepuce therethrough without dislocating the central tubular body, whereafter the removable clips may simply be re-applied, rendering the device reusable.

Accordingly, there is scope to address the aforementioned disadvantages and problems, or at least to provide a useful alternative to the known circumcision devices, aids or assistance instruments.

The preceding discussion of the background to the invention is intended only to facilitate an understanding of the present invention. It should be appreciated that the discussion is not an acknowledgment or admission that any of the material referred to was part of the common general knowledge in the art as at the priority date of the application.

SUMMARY OF THE INVENTION

In accordance with an aspect of the invention there is provided a circumcision device comprising: a support having a glans penis locating member mountable thereto, the support being provided with at least one pillar that includes a proximal end and a distal end, the distal end being fastened to a crush plate, the pillar facilitating movement of the crush plate relative to the support;

a locking device that is moveable between a locked position and an unlocked position, such that axial movement of the pillar relative to the support is inhibited in the locked position and enabled in the unlocked position, the locking device being at least partially hidden by the support; and a blocking device interposed between the support and the crush plate, and sized to block movement of the crush plate towards the support past a predefined point to inhibit the locking device from becoming exposed.

Further features may provide for the blocking device to include a proximal edge; and for the proximal edge of the blocking device to be configured to abut with the support when the crush plate is moved closer to the support by the pillar, thereby blocking, arresting or jamming further movement of the crush plate past the predefined point to inhibit the locking device from becoming exposed. Alternatively, the blocking device may include a distal edge as well as a proximal edge; and the distal edge of the blocking device may be configured to abut with the crush plate while the proximal edge of the blocking device may be configured to abut with the support when the crush plate is moved closer to the support by the pillar, thereby blocking, arresting or jamming further movement of the crush plate past the predefined point to inhibit the locking device from becoming exposed.

Still further features may provide for the locking device to be at least partially hidden inside an aperture of the support; or for the locking device to be at least partially hidden or shielded by the support; or for the locking device to be at least partially hidden or shielded by one of the pillars; alternatively, for the locking device to be entirely hidden from view.

Yet further features may provide for the device to include a pair of pillars; for the pair of pillars to be adjustable pillars; and for the proximal end of each of the adjustable pillars to include a handle for adjusting the pillars.

Further features may provide for a pair of blocking devices to be provided; for the blocking device to be a sleeve; for the pair of blocking devices to be a pair of sleeves locatable over each of the adjustable pillars; and for each of the blocking devices to be axially moveable.

Still further features may provide for the blocking device to be fixed to the support, or fixed to the crush plate, or for the blocking device to be slidably moveable relative to the pillars, alternatively for the blocking device to form part of the crush plate, or for the blocking device to form part of the support, or for the blocking device to be a separate rim or formation which is permanently attached to the at least one pillar.

A yet further feature may provide for the locking device to be a locking clip.

Further features may provide for a pair of locking devices to be provided, with each of the pair of locking devices or locking clips being configured to inhibit axial movement of each of the pair of adjustable pillars in a locked position of each locking device, and to enable axial movement of each of the pair of adjustable pillars in an unlocked position of each locking device. The locked position of each locking device may be a permanent locked position. The unlocked position of each locking device may be a temporary unlocked position.

Still further features may provide for the support to include a pair of apertures corresponding to the pair of adjustable pillars; and for the support to include a protrusion internally of each of the pair of apertures to cooperate with a recess of each of the locking devices in the locked position.

Yet further features may provide for the pair of adjustable pillars to be located on opposite sides of the support, for example on diametrically opposed sides thereof.

Further features may provide for the pair of adjustable pillars to each include an externally threaded portion; and for each of the pair of apertures to include a cooperating internally threaded portion.

Still further features may provide for each of the locking devices to be at least partially hidden, shielded, or covered inside each of the apertures of the support; and for the locking device to be at least partially hidden or shielded by one of the pillars.

Yet further features may provide for the blocking device to be configured to block or arrest movement of the crush plate towards the support past the predefined point once the device is assembled and/or prior to intended use of the device, thereby inhibiting the locking device, or the pair of locking devices, from becoming exposed or partially exposed, or from being tampered with;

and for the blocking device to be arranged to restrict movement of the locking device within a predefined region inside the support, thereby inhibiting tampering with the locking device and inhibiting reuse of the circumcision device Further features may provide for the crush plate to be made of metal such as stainless steel; for the blocking device to be made of plastics; alternatively, for any of the components of the circumcision device to be made of plastics or injection moulded plastics, or polymers, or metals, or composites, or any other suitable material or combinations of the aforesaid materials.

Embodiments of the invention will now be described, by way of example only, with reference to the accompanying drawings.

DETAILED DESCRIPTION WITH REFERENCE TO THE DRAWINGS

Figure 1:
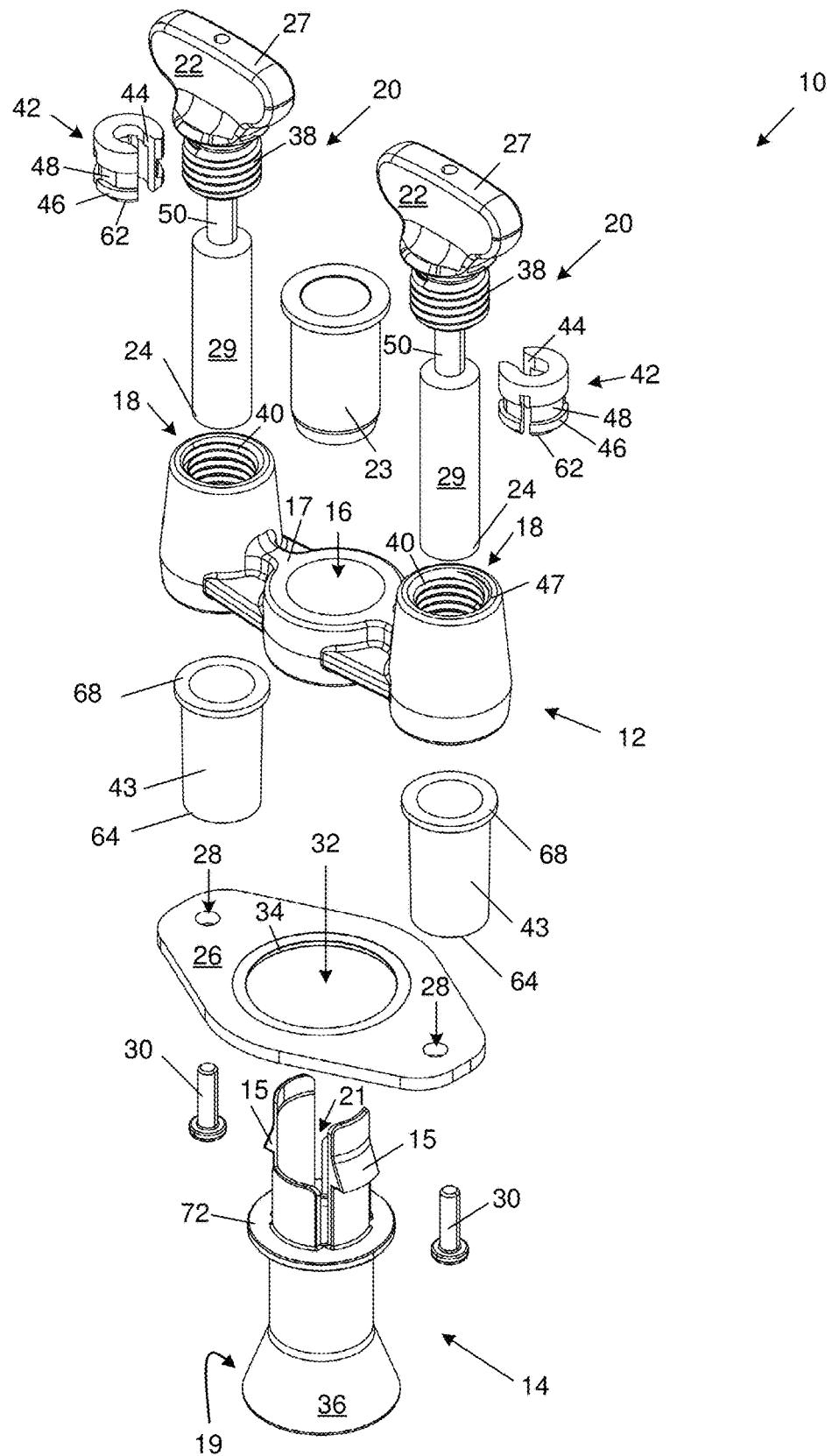
FIG. 1 is an exploded three-dimensional view of an example embodiment of a circumcision device or aid, showing various components of the device when disassembled.

Example embodiments of a circumcision device (10, 100) are illustrated in the drawings. Like features or components may be designated by like numerals in the drawings. The circumcision device may also be referred to as a circumcision aid, a surgical assistance device, or a surgical assist instrument for use during a circumcision.

Referring to the exploded three-dimensional view in FIG. 1, in an example embodiment, the circumcision device (10) may include a support (12) or holding structure, having a glans penis locating member (14) mountable thereto. The support (12) may include a central aperture (16) whereto, or inside which the locating member (14) may be mounted in use. The glans penis locating member (14) may also be referred to as a locating tube. The support (12) may include at least one aperture (18) for receiving at least one pillar (20). In the example embodiment depicted in FIG. 1, the support (12) includes a pair of opposite apertures (18) or holes for receiving a pair of adjustable pillars (20). Each of the adjustable pillars (20) may include a proximal end (27) that may have a handle (22) thereat, and a distal end (24) remote from the handle (22). Each of the one or more pillars (20) may also be referred to as a rod or a bar, or an adjustable rod or an adjustable bar, or a bolt. A crush plate (26) may be provided, and the distal ends (24) of each of the pillars (20) may be fastened to the crush plate (26). Holes (28) may be provided in the crush plate (26), wherethrough fasteners (30) may extend to fasten the pillars (20) to the crush plate (26). The pillars (20) are preferably permanently fastened to the crush plate (26) and may be inhibited from moving axially relative to the crush plate (26). The pillars may, however, be rotatable relative to the crush plate (26) about their respective major axes (54) (shown in the sectional view in FIG. 5). The fasteners (30) may be fixed to the distal ends (24) of each of the pillars (20), and they may permanently restrict or prevent axial movement of the pillars (20) relative to the crush plate (26), but the fasteners themselves may be rotatable inside the holes (28) as the pillars (20) may rotate in use.

The crush plate (26) may include a central aperture (32) and may define a crushing surface (34) or crushing rim. The pillars (20) may enable, or may facilitate movement of the crush plate (26) relative to the support (12) to facilitate crushing of a prepuce between a diverging outer surface (36) of the locating member (14) and the crushing surface (34) of the crush plate (26). As is evident from FIG. 5, the glans penis locating member (14) may be held by the aperture (16) in the support (12) and it may be held stationary relative to the support (12) as the pillars (20) move the crush plate towards the support. Movement of the pillar(s) (20) (and corresponding movement of the crush plate (26) which is attached to the one or more pillar(s)(20)) may facilitate closing a gap (52) between the crush plate (26) and the divergent outer surface (36) of the glans penis locating member (14) to crush the prepuce between the crushing surface (34) of the crush plate and the divergent outer surface (36) of the glans penis locating member (14). Referring again to FIG. 1, the pillars (20) may each include an externally threaded portion (38) for cooperating with an internal thread (40) of each of the opposite apertures (18) of the support (12), to provide axial movement of each of the pillars (20) relative to the support (12), in use. The pair of opposite apertures (18) may thus correspond to the pair of adjustable pillars (20). The glans penis locating member (14) may also be referred to as a tube or a central tube, or a tubular member. It should be appreciated that embodiments may be possible that include a single pillar, and a single corresponding aperture in the support may be provided for the single pillar.

Figure 2:
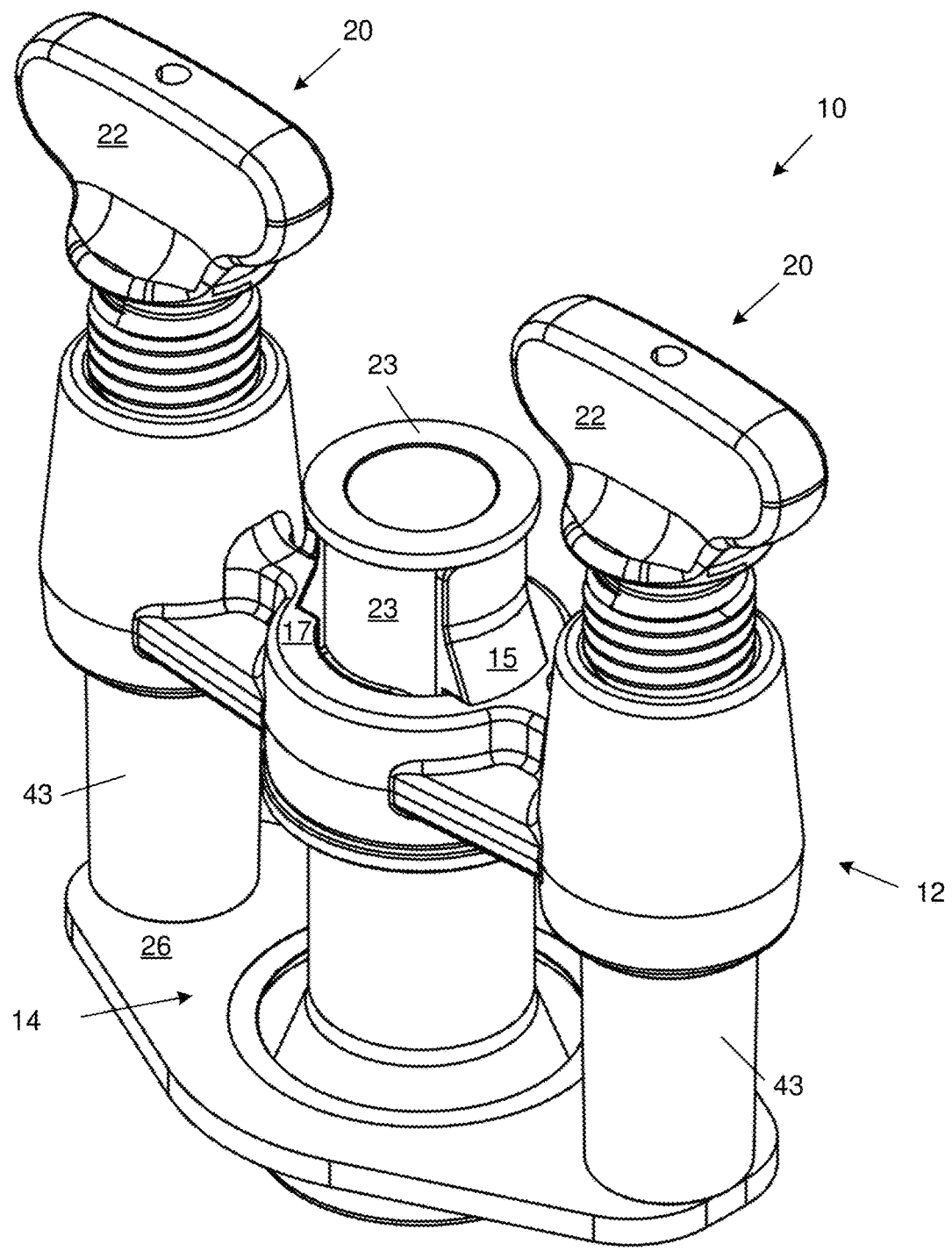
FIG. 2 is a three-dimensional view of the circumcision device of FIG. 1, showing the components assembled to one another.

The glans penis locating member (14) may include one or more wedged members (15) which snap or clip onto a proximal, operating surface (17) of the support when the glans penis locating member (14) is inserted into the central aperture (16) of the support (12) as is shown in the assembled three-dimensional view of the device in FIG. 2. The glans penis locating member (14) may be inserted from a side of the support (12) which faces the crush plate (26), through the aperture (32) in the crush plate, and through the central aperture (16) in the support, until the wedged members (15) snap or click into their positions as shown in FIG. 2, so that the glans penis locating member (14) is held by the support (12).

The glans penis locating member (14) may be transparent or translucent to facilitate positioning and alignment of the glans, to prevent or inhibit inadvertent damage thereto during a circumcision procedure (i.e. to protect the glans). The glans receiving portion (19) may for example be bell-shaped, dome-shaped, or may have a general cross-sectional shape resembling a frustum. An opening (21) or cavity may be provided in the glans penis locating member (14) for receiving a removable stop (23) or plug, which may inhibit the glans penis locating member (14) from becoming dislodged or dislocated from the central aperture (16) during crushing of a prepuce in use. As is evident from FIG. 2, the stop (23) or plug may temporarily prevent the wedged members (15) from being undone while the circumcision procedure is performed. In other words, the stop (23) or plug may inhibit the wedged members (15) from moving towards one another when they are in the configuration or position shown in FIG. 5, thereby inhibiting or preventing the glans penis locating member (14) from being released from the aperture (16) wherein it is held during crushing of a prepuce.

Referring again to FIG. 1, the circumcision device (10) or circumcision aid may further include one or more locking devices (42). Preferably, a pair of locking devices (42) are provided, one for each of the pillars (20). Each of the locking devices may be a locking clip (42) and may include a slot (44), a peripherally extending rim (46), and a recess (48). In the present embodiment, the locking clips (42) are locatable to a narrow or thin portion (50) of each of the adjustable pillars (20). As shown in FIG. 2, once the device (10) is assembled, the locking devices (42) may be at least partially hidden, covered or shielded to inhibit or prevent tampering. In the present embodiment, the locking devices are provided internally of the opposite apertures (18) and are therefore hidden or concealed from view by a body of the support (12) and/or by each of the pillars (20). Each of the locking devices (42) may be hidden or concealed between the support (12) and the pillar (20) as shown in the sectional view in FIG. 5. Each of the locking devices (42) may also be entirely hidden as is shown in FIG. 2 (i.e. the locking device(s) (42) are not visible in FIG. 2). The device (10) may be pre-assembled in a configuration similar to FIG. 2 (for example during manufacturing), so that the locking devices (42) are not visible to a user of the device (10). One or more blocking devices (43) may be provided or interposed between the support (12) and the crush plate (26). The blocking devices may be sleeves, however other types of blocking devices may also be used as described below. Each of the blocking devices (43) may be configured to block or arrest movement of the crush plate (26) towards the support (12) past a first predefined point (45) (shown in FIGS. 5 and 6), to inhibit the one or more locking devices (42) from becoming exposed. Each blocking device (43) may be sized, shaped or configured to block movement of the crush plate towards the support past the first predefined point (45). This may inhibit or prevent tampering with the locking devices (42) and it may render the circumcision device (10) a single-use device. Stated differently, the one or more blocking devices (43) may limit movement of the one or more locking devices (42) to a predefined region (79) (see FIG. 5) inside a body of the support (12). The operation of the blocking devices (43) is described in more detail below.

Figure 3:
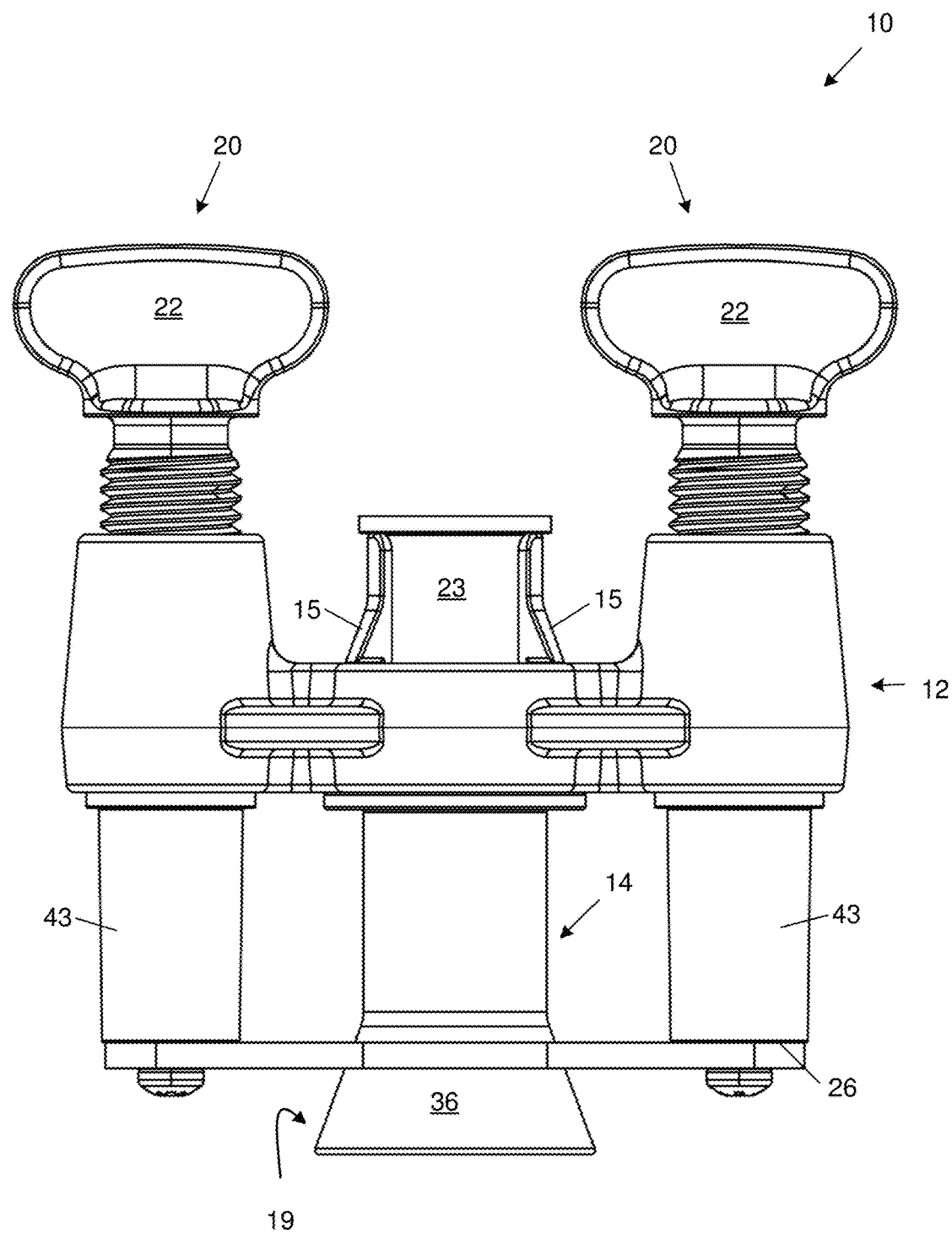
FIG. 3 is a front view of the circumcision device showing a pair of adjustable pillars and a pair of blocking devices.
Figure 4:
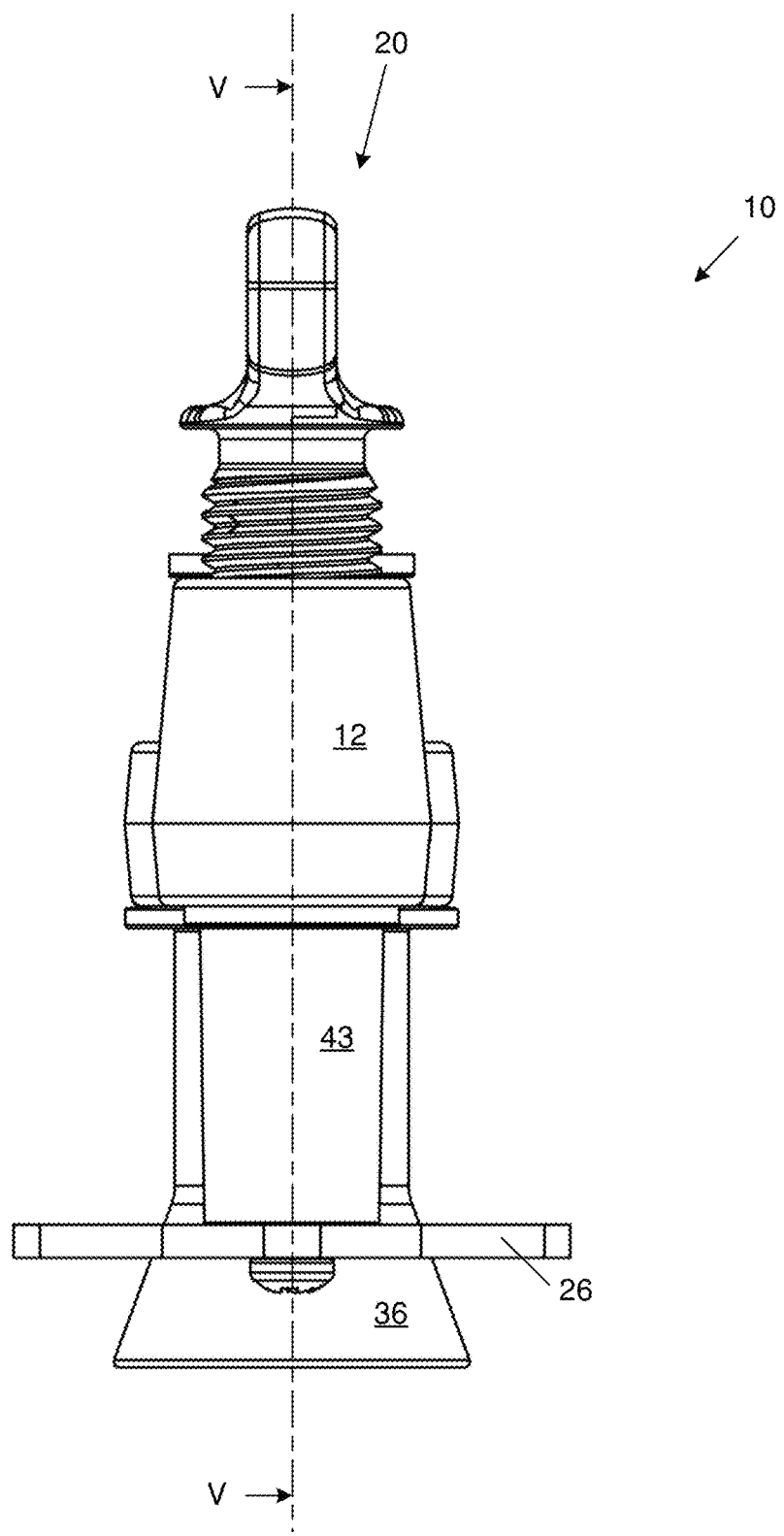
FIG. 4 is a side view of the circumcision device.
Figure 5:
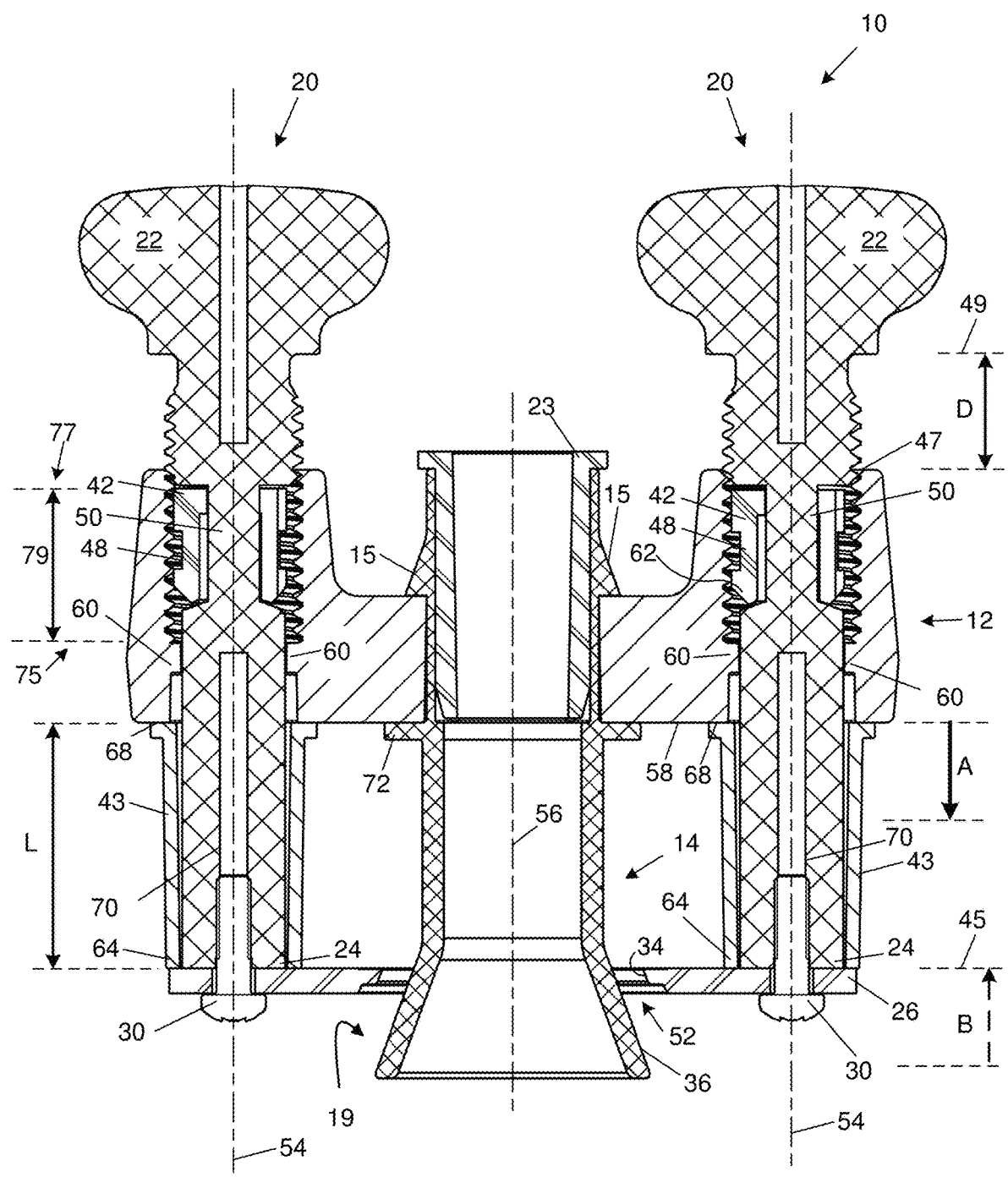
FIG. 5 is a sectional view taken along line V-V in FIG. 4, showing internal locking clips, as well as corresponding protrusions.
Figure 6:
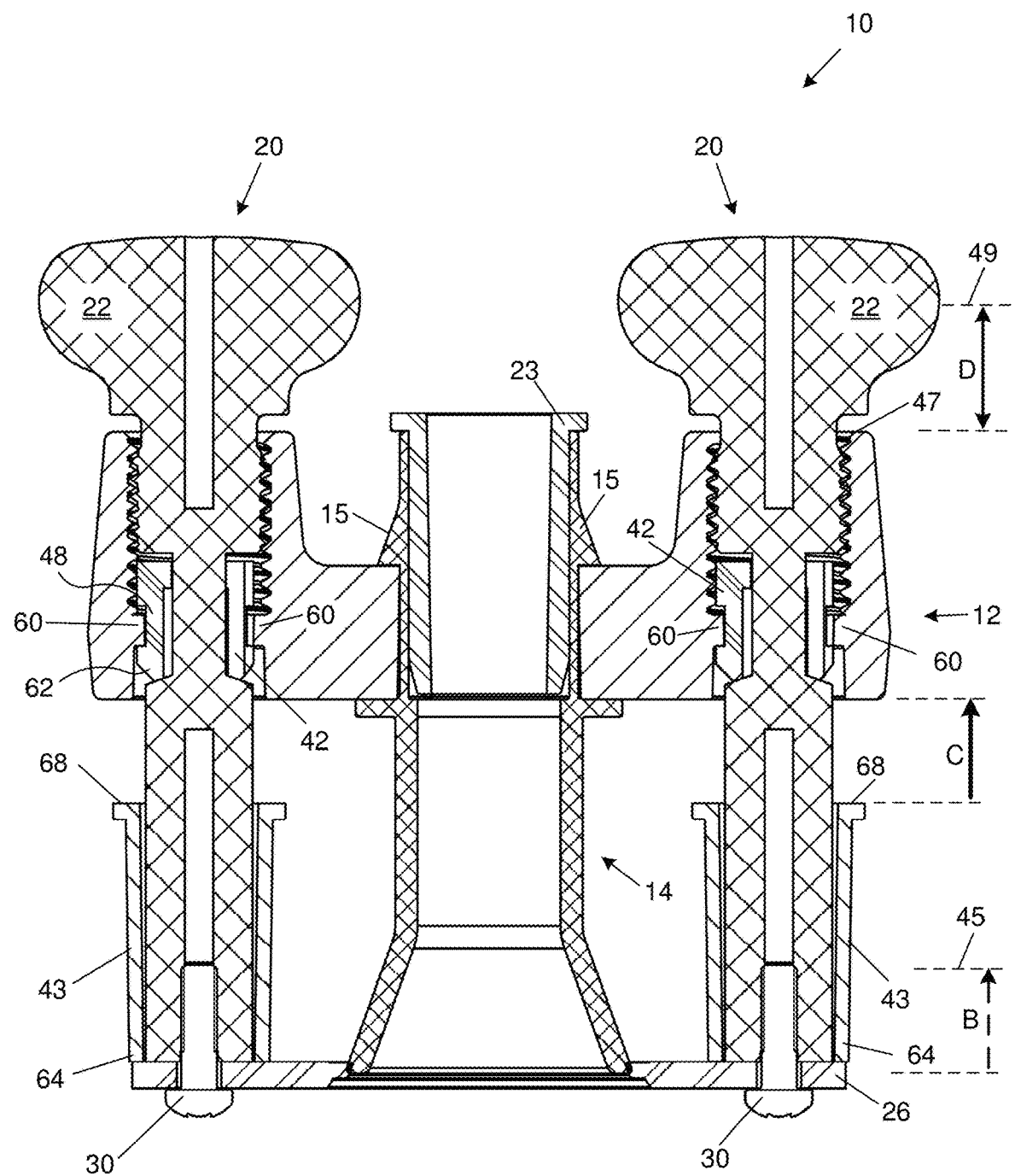
FIG. 6 is a sectional view similar to FIG. 5, however showing the adjustable pillars after they have been adjusted to perform crushing, and also showing the clips that have engaged with the protrusions to lock the pillars in place.

FIGS. 3 and 4 show an exemplary embodiment of an assembled circumcision device (10) or circumcision aid as viewed from the front and side respectively. It will be appreciated that the device may be used to facilitate circumcisions and it may also be referred to as a surgical assistance device or a surgical assistance apparatus. FIG. 5 shows a sectional view taken along line V-V in FIG. 4 and shows the pillars (20) when they are adjusted such that the glans penis locating member (14) is in an open position relative to the crush plate (26). A closed position, or crushing position is shown in FIG. 6. FIG. 5 also illustrates the glans penis locating member (14) inserted into the central aperture (16) of the support (12) and clipped or snap-fitted thereto.

In this open position of the glans penis locating member (14), a prepuce may be positioned or folded over the diverging outer surface (36) and through the gap (52) between the crush plate (26) and the outer surface (36), so that the prepuce may be crushed by the crushing surface (34) of the crush plate (26) while the glans is held and protected inside the glans receiving portion (19). As described above, crushing may be facilitated by adjusting the adjustable pillars (20), for example by turning the handles (22) to move each of the pillars axially. The glans may thus be protected by the glans receiving portion (19) during circumcision. Once the prepuce is crushed, it may be cut away, for example by cutting it on a proximal or upper side of the crush plate (26) that faces the support (12).

Referring to FIG. 5, the adjustable pillars may thus be axially moveable along their respective major axes (54) which may cause the crush plate (26) to move generally along a major axis (56) of the glans penis locating member (14). In other words, if the adjustable pillars (20) are adjusted for crushing, they may move in the direction of directional arrow (A) (relative to the support (12)), and the thin portion (50) with the clip (42) thereon may also move in the direction of directional arrow (A), or towards a distal surface (58) of the support (12) that faces the crush plate (26). The locking devices (42) are moveable between an unlocked position (shown in FIG. 5) and a locked position (shown in FIG. 6). In the present embodiment, protrusions such as annular protrusions (60) may be provided inside each of the opposite apertures (18) of the support (12). The pair of adjustable pillars (20) may be located on opposite sides of the support (12), for example on diametrically opposed sides thereof, or on diametrically opposite sides of the central aperture (16). In the unlocked position, which may be a temporary unlocked position, each pillar (20) may be freely rotatable, and hence moveable in an axial direction, as the locking devices or clips (42) are held by the narrow or thin portions (50), but the clips are able to move axially to a limited extent. The clips or locking devices (42) may also be freely rotatable about the major axis (54) of each of the pillars (20) and about the thin portions (50), but the locking devices (42) may prevent or inhibit axial movement of the pillars (20) once they are in their locked positions (as shown in FIG. 6).

The blocking device (43) may block, inhibit or prevent the locking device (42) of each pillar (20) from being withdrawn from the support (12) past a second predefined point (77), and this may in turn prevent or inhibit the locking devices (42) from becoming exposed and/or being tampered with. Referring to FIGS. 5 and 6, a first predefined point may be defined as a point (45) between the crush plate (26) and the support (12), and this may be a limit of movement of the crush plate (26). A second predefined point (49) may be defined as a point (49) measured from a proximal or upper edge (47) of the support (12). The blocking device (43) may prevent or inhibit the head or handle (22) of the pillar (20) from being withdrawn past the second predefined point (49). As seen in FIGS. 5 and 6, the second predefined point (49) may be located at a distance (D) of travel or movement of the pillar (20) which may be reached once the blocking device (43) comes into abutment with the lower or distal surface (58) of the support (12) as the pillar (20) is moved in a direction of the directional arrow (C). The first predefined point (45) is also shown in FIG. 5 ant it may be a predefined point (45) or limit of movement of the crush plate (26) towards the support (12). The blocking device (43) may yet further inhibit or prevent movement of the locking device (42) past a third predefined point (77) (see FIG. 5). The third predefined point (77) may be referred to as a predefined limit, or a predefined upper boundary (77) or a proximal boundary that is located at a proximal end of a region (79) inside each aperture (18). The region (79) may for example extend from the protrusions (60) of the support (12) in a direction of the axis (54) of the pillar (20), and the region may also include a predefined lower boundary (75), or distal boundary. The pillar (20) and the locking device (42) may thus be axially moveable as long as the clip or locking device (42) is within the bounds of this region (79) inside the aperture (18). The locking devices or locking clips (42) may be concealed, hidden or covered while they are inside this region (79) inside the support (12), or inside the aperture (18). The region (79) may be predefined or predetermined. The blocking device or blocking devices (43) may be arranged to restrict movement of the locking device or locking devices (42) within this predefined region (79) inside the support (12). In other words, each blocking device (43) may inhibit or block each locking device (42) from being withdrawn from the support (12) past the third predefined point (77), alternatively the blocking device (43) may prevent or inhibit the crush plate (26) from moving past the first predefined point (45), alternatively the blocking device (43) may prevent or inhibit the pillar (20) (or its handle (22) or head) from being withdrawn past the second predefined point (49).

Referring to FIGS. 5 and 6, As the clips or locking devices (42) are moved by the pillars (20) in the direction of directional arrow (A), the recesses (48) (also shown in FIG. 1) may eventually snap or click over the protrusions (60), and an audible "click" sound may be produced. Chamfers (62) or other wedged or angled formations may be provided on the clips to facilitate the clips to snap over the annular protrusions (60). Hence, when the crush plate (26) is moved away from the support (12) in the direction of directional arrow (A) by adjusting the pillars (20) to perform crushing, the clips may eventually reach the locked position as shown in FIG. 6, in which the recesses (48) are located over, and become locked by the protrusions (60). The locked position may be a permanent locked position, as a user of the device may not be able to remove the pillar in the permanent locked position of the locking device (or without breaking, substantially damaging or destroying the circumcision device or aid (10), or parts thereof). This may dissuade a user from attempting to reuse the device, which may inhibit the spread of infection. The recesses (48) and protrusions (60) may be complementarily shaped. When the locking devices or clips (42) are in this locked position, they may inhibit further axial movement of the pillars (20) relative to the support (12) (save for a limited amount of movement as result of selected tolerances). On the other hand, axial movement of the pillars (20) may be enabled when the clips or locking devices are in the unlocked position as shown in FIG. 5 (i.e. within the confines of the region (79) in FIG. 5). It will be appreciated that the clips or locking devices (42) are at least partially hidden, concealed, or shielded to inhibit tampering, as is evident from FIGS. 2 to 6. It will further be appreciated that the locking devices may alternatively form part of each pillar. For example, the recess (48) may be a recess which is integrally formed in or on each pillar (20).

FIG. 6 shows a sectional view similar to FIG. 5, however showing the adjustable pillars after they have been adjusted to perform crushing, with the clips (42) having engaged with or clicked over the protrusions (60). The blocking devices (43) may be sleeves which may be loosely fitted or located over distal portions (29) of the pillars (20) (shown in FIG. 1). Each blocking device (43) may include a distal edge or surface (64) and a proximal edge or surface (68). In the case of the blocking device being a sleeve, a flange may be provided at the proximal edge or surface (68) to facilitate abutment with the distal surface (58) of the support (12). The distal edge (64) of the blocking device (43) may, in turn, be configured to abut with the crush plate (26) and the proximal edge (68) of the blocking device (43) may be configured to abut with the support (12) when the crush plate (26) is drawn closer to the support (12), in a direction of dashed arrow (B) in FIGS. 5 and 6 by the adjustable pillars (20). The aforesaid movement of the crush plate (26) in the direction of dashed arrow (B) may only be possible when the locking devices or clips (42) are in the unlocked position. A further optional flange (not shown) may also be provided at the distal edge (64) of the blocking device (43).

Still referring to FIGS. 5 and 6, the blocking devices (43) may thus block or jam movement of the crush plate (26) towards the support (12) past the first predefined point (45) or level, thereby inhibiting the locking devices (42) from becoming exposed. After the crush plate (26) is moved a distance as indicated by dashed arrow (B), the locking devices (42) may still be at least partially shielded, covered or hidden by the support (12) as is evident from FIG. 5. Stated differently, the blocking devices (43) may block movement of the pillars (20) along their major axes (54), past the second predefined point (49) or level, or the blocking devices (43) may block movement of the pillars (20) past the first predefined point (45) or level. As long as the locking devices (42) are in the unlocked position (i.e. not engaging the protrusions (60)), the crush plate (26) may be enabled to be moved by the adjustable pillars (20) towards the support (12), until it reaches the first predefined point (45) which may be reached when the support plate (26) has moved a distance as illustrated by the dashed arrow (B) in FIGS. 5 and 6. Hence, each of the blocking devices (43) may be moved by the crush plate (26) (i.e. indirectly moved by the pillars (20)) up to a distance illustrated by the solid arrow (C) in FIG. 6 (provided that the clips (42) have not locked, snapped, clicked, engaged or clipped onto the protrusions (60) yet). Once the locking device or clip (42) is engaged with the protrusion (60), the crush plate (26) may not be able to move towards the support (12) or away from the support anymore, because the pillars cannot be rotated (or they cannot be rotated enough to cause or actuate substantial movement of the crush plate (26)). In the present embodiment, this is because the locked clips may inhibit axial movement of the pillars and thus also inhibit movement of the crush plate (26)). In the present embodiment, the blocking devices (43) may thus inhibit or prevent movement of the crush plate (26) closer to the support (12) than a length (L) of the blocking devices. The length (L) may be a predefined length. Before each of the clips (42) are engaged with the respective protrusion (60), and when they are still on the side of the protrusion (60) as shown in FIG. 5 (i.e. within the region (79)), the crush plate (26) may be able to move both towards the support and away from the support (but only up to a predetermined distance indicated by directional arrow (A).

When the crush plate is moved the distance of dashed arrow (B) towards the support (12), the proximal edge (68) of the blocking device (43) may abut with the support (12) and the distal edge (64) may abut with the crush plate, thereby inhibiting, blocking or jamming further movement of the crush plate (26) beyond the first predetermined point (45) towards the support (12) and thus inhibiting the locking devices (42) from becoming exposed. As shown in FIG. 5, the locking devices may be hidden by the support (12) and may hence be shielded, protected or concealed. Once the device (10) is assembled as shown in FIG. 2, the blocking devices may prevent or inhibit the pillars from being withdrawn from the support (12) and may hence inhibit tampering with the locking devices (42). Further tamper resistance may be provided by permanently affixing the crush plate (26) to each of the pair of adjustable pillars (20). This may be done by using fasteners (30) such as security screws, tamper resistant fasteners, or one-way screws which can only be screwed in and which resist tampering or loosening. Screws or fasteners with unusual heads may be used (i.e. screws that do not have conventional Philips, flat or hexagonal sockets in their heads). Another way of permanently fastening the crush plate (26) to the pillars (20) may be by utilising glue or adhesive between the fasteners (30) and corresponding holes (70) in the pillars (20) (shown in FIG. 5), or by machining away part of the head of the fastener after it has been installed or fastened, to inhibit it from being unscrewed or removed. Alternatively, other permanent fastening mechanisms may be used to rotatably secure the pillars to the crush plate (i.e. enabling rotation of the pillar (20) relative to the crush plate (26), but securing the pillar (20) so as not to move axially relative to the crush plate (26)). For example, the fasteners may be press fitted or friction fitted inside the holes (70) in the pillars (20).

Referring again to FIG. 6, when crushing of the prepuce has been performed and the prepuce has subsequently been cut away, the stop (23) may be removed. A user of the device (10) or aid may then press the wedged members (15) of the glans penis locating member (14) inwardly (i.e. the wedged members (15) may be pressed towards one another) to release, dislodge or dislocate the glans penis locating member (14) from the central aperture (16) of the support (12). Once released, the glans penis locating member (14) may be separated from the rest of the device (10). However, the glans penis locating member (14) may be inhibited from being re-inserted into the central aperture (16), as the locking clips (42) are in the locked position which inhibits the adjustable pillars (20) to move axially. This is because manual manipulation of the dislocated glans penis locating member (14) would not easily cause the wedged members (15) to be pressed enough into the central aperture (16) to snap or click back onto the proximal, operating surface (17) of the support (12) as it would require a substantial amount of force to push the diverging outer surface (36) far enough through the central aperture (32) of the crush plate (26). Nonetheless, even if somehow a user is able to manipulate the dislocated glans penis locating member (14) back into the position (or configuration) shown in FIG. 6, there would not be a gap (52) (as in FIG. 5) for receiving a subsequent prepuce, or the gap would be too small.

Therefore, the locking devices (42) may inhibit the circumcision device (10) or circumcision aid to be reused after crushing has been performed. The blocking devices (43), in turn, may inhibit the device (10) to be tampered with before (or after) crushing is performed. The blocking devices (43) may also prevent or inhibit the device (10) to be unscrupulously reused. As shown in FIG. 5, once the circumcision device or aid (10) is assembled and the blocking devices (43) are in place, they may block movement of the crush plate (26) past the first predefined point (45) or level, and hence a user may not be able to unscrew or withdraw the pillars from the opposite apertures (18) and the user may be prevented or inhibited from accessing or exposing the locking device(s) (42). Unwanted tampering or removal of the locking devices (42) may thus be prevented or inhibited. As shown in FIG. 5, the glans penis locating member (14) may include a flange (72) which may abut with the distal surface (58) of the support (12) that faces the crush plate (26), when the glans penis locating member (14) is installed in the central aperture (16) of the support (12). The flange (72) may facilitate the glans penis locating member to be held captive by the aperture (16) while a circumcision is performed.

Figure 7:
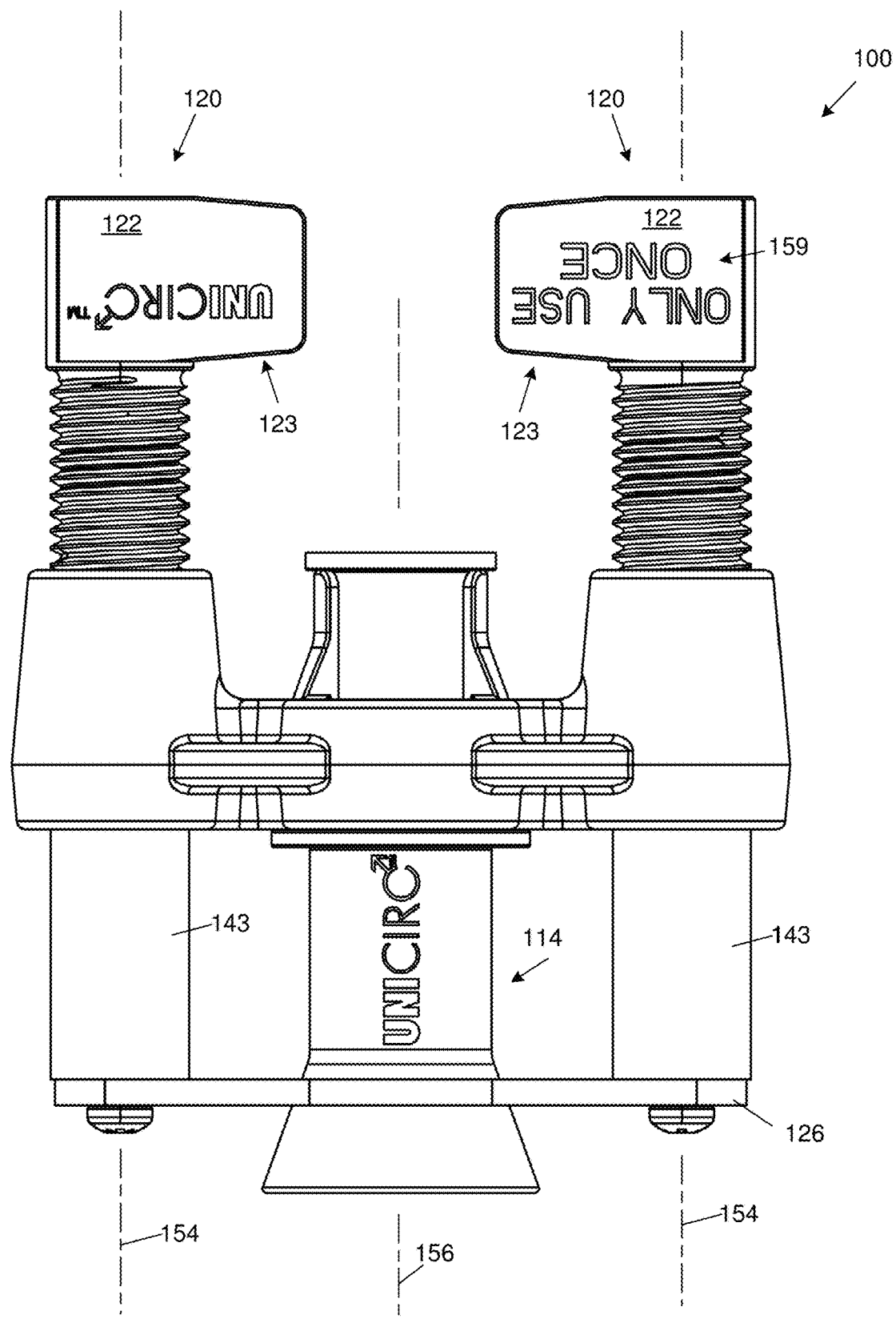
FIG. 7 is a front view of another embodiment of the circumcision device.

In FIG. 7 is shown another exemplary embodiment of a circumcision device (100), which may also be referred to as a circumcision aid, or a surgical assist circumcision instrument. In the present embodiment, the device or aid (100) may also include pillars (120), but the pillars may be longer than those depicted in FIGS. 1 to 6, in a direction of their major axes (154). The pillars (120) may also include handles (122) or heads that are elongated in a direction transverse to the major axes (154), and the handles (122) may include elongated portions (123). Indicia (159) may be applied to the handles, or other parts of the device (100), for example the words "only use once", so that it is clear that the device should only be used once, and it should preferably be safely discarded, destroyed or incinerated after use to prevent or inhibit the transfer of infection. The circumcision device (100) may also include blocking devices (143) to facilitate or implement non-reusability as described herein. The components of the circumcision device or aid (100) may be similar to the components described with reference to FIGS. 1 to 6, apart from the elongated handles, the longer pillars, and the blocking devices (143) that are slightly different in shape in this particular embodiment. In the present embodiment shown in FIG. 7, a straight blocking device (143), or a pair of straight blocking devices, or sleeves may be used (in other words, the flange at the proximal edge or surface (68) of the blocking device shown in FIG. 1 may be omitted). A glans penis locating member (114) may be provided in the present embodiment (100), which may be similar to the glans penis locating member or tube (14) described above with reference to FIGS. 1 to 6. A crush plate (126) may also be similar to the crush plate (26) described above.

Figure 8:
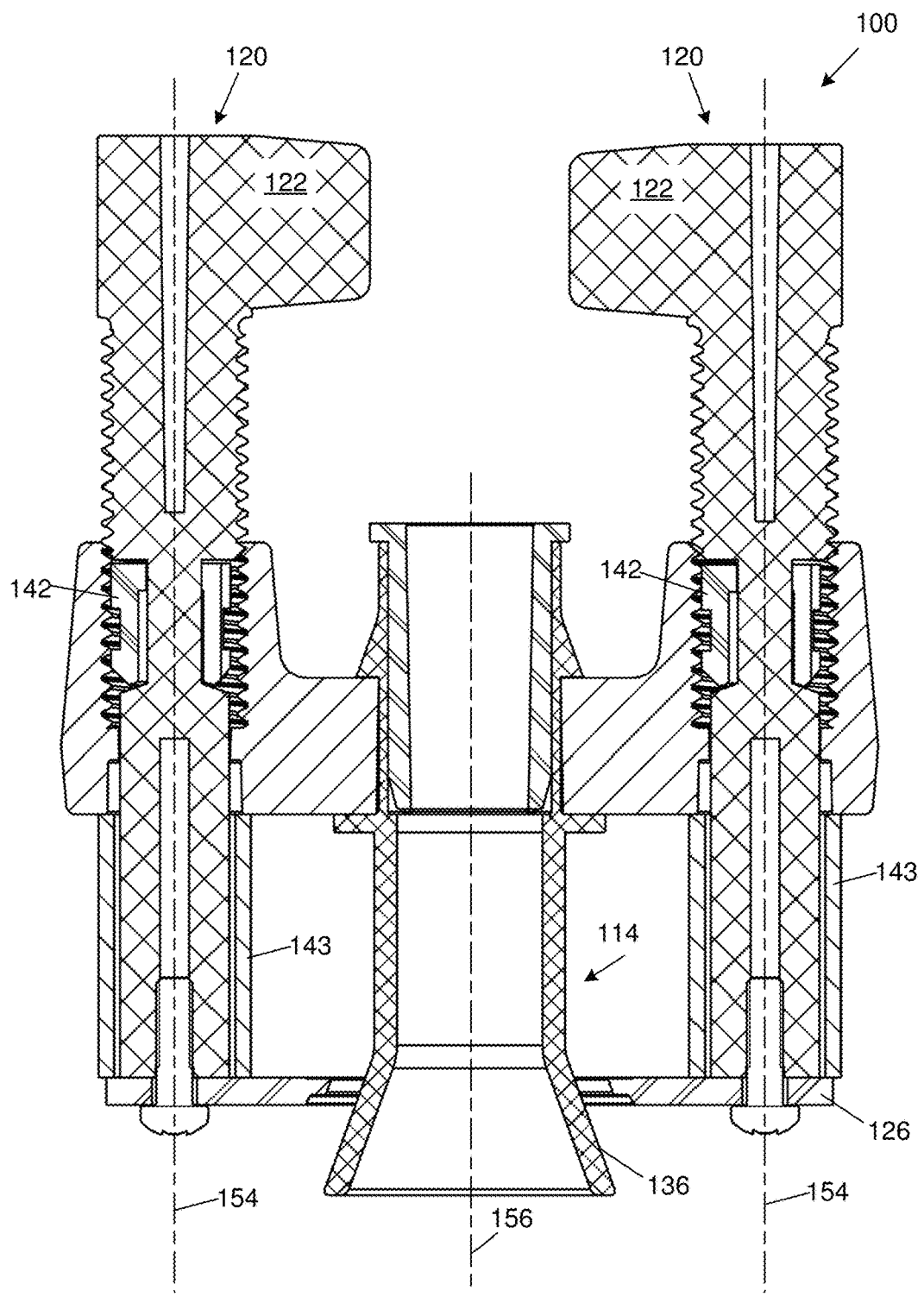
FIG. 8 is a sectional view of the circumcision device of FIG. 7.

FIG. 8 shows a sectional view taken through the major axes (154) of the pillars and through a major axis (156) of the glans penis locating member (14). The functionality of locking devices (142) may be similar to the functionality of the locking devices (42) described with reference to FIGS. 1 to 6. The elongated pillars (120) and the elongated handles (122) may facilitate use of the device or aid (100), and this may facilitate a circumcision procedure, as a user of the device may manipulate the handles more easily, or with more force because a greater moment may be applied to the pillars using the elongated handles. This may in turn cause more force to be applied to the crush plate, and more force may thus be applied to an interface between the crush plate (126) and the diverging outer surface (136) of the glans penis locating member (114). It will be appreciated that the embodiment shown in FIGS. 7 and 8 may include some or all of the features of the other embodiments described herein (for example, features of the embodiment of FIGS. 1 to 6). It will also be appreciated that the embodiment shown in FIGS. 1 to 6 may include some or all of the features of the embodiment of FIGS. 7 and 8, or some or all of the other features described herein.

The foregoing description has been presented for the purpose of illustration; it is not intended to be exhaustive or to limit the invention to the precise forms disclosed. Persons skilled in the relevant art can appreciate that many modifications and variations are possible in light of the above disclosure.

For example, the circumcision device may include a pair of blocking devices or sleeves or a single blocking device or sleeve. A pair of locking devices or locking clips, or a single locking device or locking clip may be provided. Opposite apertures of the support need not necessarily be opposite to one another, and may for example be adjacent to one another. The support may have a variety of shapes and is not limited to the exemplary shape shown in the Figures. The one or more blocking or jamming devices may also be elongated elements that are sized to extend between the support and the crush plate, and the blocking devices need not be shaped as sleeves. The blocking devices may be sized to block movement, and need not extend a substantial distance between the support and the crush plate. For example, a blocking device such as a blocking protrusion or formation may be provided on one or more of the pillars, which blocking formation may include a proximal edge which may abut with the distal side of the support during blocking. The crush plate may be manufactured from metal such as steel, stainless steel or surgical stainless steel, and the other components of the device may be manufactured from plastics, or injection moulded plastics. Other materials, polymers, metals, or composite materials or combinations of these may be used. The circumcision device may be sterilised after it is manufactured and packaged in a sterilised container. It will be appreciated that variations are possible that incorporate any of the above features in combination with the other features described herein.

An embodiment may be possible wherein the locking device or locking clip is integral to the pillar. The recess may for example be a recess that is provided in the periphery of the pillar, which recess may cooperate with the protrusions in the aperture of the support. In other words, the locking device may be the pillar itself, or part of the pillar may function as a locking device to arrest movement of the pillar relative to the support in a locked position, and movement of the pillar may be enabled in an unlocked position. It will be appreciated that variations are possible that incorporate any of the above features in combination with the other features described herein. The circumcision device may include the pair of pillars as is illustrated in the Figures, however, embodiments are possible wherein a single pillar is utilised. A single blocking device may be provided in respect of the single pillar (or for one or more of the pillars) for blocking movement of the crush plate relative to the support. The blocking devices illustrated may be one or more loose sleeves which may be slidably located over the pillars so that they may slide freely. However, embodiments are possible wherein the one or more blocking devices are fixed to the crush plate, or fixed to the support. The blocking device may also form part of the crush plate or may form part of the support, and may be a projecting part which extends between the crush plate and the support that may block movement of the crush plate towards the support past the predefined point. The blocking device may also be a projecting rim, a projecting formation or a projecting member which extends from a periphery of one or both of the pillars. The blocking device may be a separate rim or formation which is permanently attached to the at least one pillar. The blocking device may be integral to one of the pillars. Alternatively, the blocking device may be permanently fastened to the pillar, for example at a location on the pillar towards the distal end of the pillar.

The blocking device may be fastened at a location on the pillar which is at a predefined distance from the distal end of the pillar. The predefined distance where such a blocking device may be fastened to the pillar may approximately correspond to the predefined length of the blocking device depicted in FIG. 5, or other distances may be selected, depending on practical considerations. It may also be possible to manufacture the pillars in two parts, with a lower or distal part including the blocking device, and with an upper or proximal part including the handle. it will be appreciated that variations are possible that incorporate any of the above features in combination with the other features described herein. The circumcision device may provide advantages over known circumcision devices that the applicant is aware of. The device may prevent or may resist tampering and may thus provide a single use device, or attempts to reuse the device may be resisted by the one or more blocking devices in combination with the one or more locking devices. The circumcision device disclosed herein may resist tampering, before and after use of the device. In embodiments of the invention, tamper resistance may be provided when the device is assembled. The circumcision device disclosed herein may provide a non re-usable, non-necrotising surgical assist instrument.

The language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon.

Accordingly, the disclosure of the embodiments of the invention is intended to be illustrative, but not limiting, of the scope of the invention, which is set forth in the following claims.

Finally, throughout the specification and accompanying claims, unless the context requires otherwise, the word 'comprise' or variations such as 'comprises' or 'comprising' will be understood to imply the inclusion of a stated integer or group of integers but not the exclusion of any other integer or group of integers.

The invention claimed is:

1. A circumcision device comprising:
   a support having a glans penis locating member mountable thereto, the support being provided with at least one pillar that includes a proximal end and a distal end, the distal end being fastened to a crush plate, the pillar facilitating movement of the crush plate relative to the support;
   a locking device that is moveable between a locked position and an unlocked position, such that axial movement of the pillar relative to the support is inhibited in the locked position and enabled in the unlocked position, the locking device being at least partially hidden by the support; and
   a blocking device interposed between the support and the crush plate, and sized to block movement of the crush plate towards the support past a predefined point to inhibit the locking device from becoming exposed.

2. The circumcision device as claimed in claim 1, wherein the blocking device includes a proximal edge which is configured to abut with the support when the crush plate is moved closer to the support by the pillar, thereby blocking further movement of the crush plate past the predefined point to inhibit the locking device from becoming exposed.

3. The circumcision device as claimed in claim 1, wherein the locking device is at least partially hidden, inside an aperture of the support.

4. The circumcision device as claimed in claim 1, wherein the circumcision device includes a pair of adjustable pillars and a pair of blocking devices.

5. The circumcision device as claimed in claim 4, wherein each blocking device is a sleeve locatable over one of the adjustable pillars.

6. The circumcision device as claimed in claim 4, wherein a pair of locking devices are provided with each of the pair of locking devices being configured to inhibit axial movement of each of the pair of adjustable pillars in a locked position of each locking device, and to enable axial movement of each of the pair of adjustable pillars in an unlocked position of each locking device.

7. The circumcision device as claimed in claim 6, wherein the support includes a pair of apertures corresponding to the pair of adjustable pillars.

8. The circumcision device as claimed in claim 7, wherein the support includes a protrusion internally of each of the pair of apertures to cooperate with a recess of each of the locking devices in the locked position.

9. The circumcision device as claimed in claim 7, wherein the pair of adjustable pillars each includes an externally threaded portion, and wherein each of the pair of apertures includes a cooperating internally threaded portion.

10. The circumcision device as claimed in claim 1, wherein the blocking device is arranged to restrict movement of the locking device within a predefined region inside the support, thereby inhibiting tampering with the locking device and inhibiting reuse of the circumcision device.

* * * * *